US012708651B2

(12) United States Patent
Bergonzelli Degonda et al.

(10) Patent No.: US 12,708,651 B2
(45) **Date of Patent: *Aug. 18, 2026**

(54) **METHODS AND COMPOSITIONS USING *BIFIDOBACTERIUM LONGUM* TO MODULATE EMOTIONAL REACTIVITY AND TREAT OR PREVENT SUB-CLINICAL MOOD DISTURBANCES**

(71) Applicant: SOCIÉTÉ DES PRODUITS NESTLÉ S.A., Vevey (CH)

(72) Inventors: Gabriela Bergonzelli Degonda, Bussigny (CH); Tiago Alves Nunes, Bern (CH); Valerie Marquardt, Epalinges (CH); Jeroen Antonius Johannes Schmitt, Moudon (CH)

(73) Assignee: Societe des Produits Nestle S.A., Vevey (CH)

( * ) Notice: Subject to any disclaimer, the term of this patent is extended or adjusted under 35 U.S.C. 154(b) by 992 days.

This patent is subject to a terminal disclaimer.

(21) Appl. No.: 16/950,493

(22) Filed: Nov. 17, 2020

(65) Prior Publication Data

US 2021/0060096 A1 Mar. 4, 2021

Related U.S. Application Data

(63) Continuation of application No. 15/754,894, filed as application No. PCT/EP2016/070465 on Aug. 31, 2016, now abandoned.

(60) Provisional application No. 62/236,638, filed on Oct. 2, 2015, provisional application No. 62/220,414, filed on Sep. 18, 2015, provisional application No. 62/212,148, filed on Aug. 31, 2015.

(51) Int. Cl.

*A61K 35/745* (2015.01)
*A23L 33/135* (2016.01)
*A61P 25/22* (2006.01)

(52) U.S. Cl.

CPC .......... *A61K 35/745* (2013.01); *A23L 33/135* (2016.08); *A61P 25/22* (2018.01); *A23V 2002/00* (2013.01); *A23V 2200/31* (2013.01); *A23V 2200/3202* (2013.01); *A23V 2200/3204* (2013.01); *A23V 2200/322* (2013.01)

(58) Field of Classification Search

CPC ....... A61K 35/745; A23L 33/135; A23L 2/52; A61P 25/22; A23V 2002/00; A23V 2200/31; A23V 2200/3202; A23V 2200/3204; A23V 2200/322; A23C 9/13; A23C 9/152; A23G 9/363; A23Y 2220/03; A23Y 2220/43; A23Y 2220/63; A23Y 2220/67; A23Y 2220/71; A23Y 2220/73; A23Y 2220/79

See application file for complete search history.

(56) References Cited

U.S. PATENT DOCUMENTS

| | | | | |
|---|---|---|---|---|
| 8,343,482 | B2 * | 1/2013 | Bergonzelli | A23L 33/135 424/93.3 |
| 10,214,745 | B2 | 2/2019 | Faghihi et al. | |
| 10,849,344 | B2 | 12/2020 | Yanamoto | |
| 2004/0265279 | A1 | 12/2004 | Dinan et al. | |
| 2010/0316619 | A1 | 12/2010 | Wittke et al. | |
| 2012/0121562 | A1 | 5/2012 | Bergonzelli Degonda et al. | |
| 2012/0177607 | A1 | 7/2012 | Mozzetti et al. | |
| 2012/0230956 | A1 | 9/2012 | McLean et al. | |
| 2013/0122151 | A1 | 5/2013 | Ghaedian et al. | |

FOREIGN PATENT DOCUMENTS

| | | | |
|---|---|---|---|
| EP | 2110028 | 10/2009 | |
| WO | 0112164 | 2/2001 | |
| WO | WO-2004098622 A2 * | 11/2004 | A61K 35/745 |
| WO | 2010060722 | 6/2010 | |
| WO | WO-2011058535 A1 * | 5/2011 | A23C 9/1234 |

OTHER PUBLICATIONS

Canbeyli, R Sensorimotor modulation of mood and depression: in search of an optimal mode of stimulation, Front. Hum. Neurosci., Jul. 30, 2013 (Year: 2013).*

Tarar et. al. Burden of anxiety and depression among hospitalized patients with irritable bowel syndrome: a nationwide analysis Irish Journal of Medical Science (1971-) https://doi.org/10.1007/s11845-022-03258-6; Oct. 16, 2022 (Year: 2022).*

Chao et al., "Neurotrophin Signalling in Health and Disease", Clinical Science, vol. 110, 2006, pp. 167-173.

Duman et al., "Neuronal Plasticity and Survival in Mood Disorders", Biological Psychiatry, vol. 48, Issue No. 8, 2000, pp. 732-739.

Wang et al., "Study on the Molecular Genetics of Depression and Interaction between Gene and Environment", Journal of Taishan University, vol. 33, Issue No. 3, May 2011, pp. 102-107.

Lin et al., "Relationship Between BDNF-TrkB Signaling Pathway and the Generation of Anxiety Disorders", vol. 33, Issue No. 6, 2013, pp. 668-672.

China Patent Office Action Received for Application No. 201680049469.1, mailed on Nov. 2, 2020, 15 pages.

Pinto-Sanchez et al. "OP162 *Bifidobacterium longum* NCC3001 Improves Depression and Reduces Brain Emotional Reactivity in Patients With Irritable Bowel Syndrome (IBS): A Randomized, Double Blend, Placebo-Controlled Trial" United European Gastroenterology Journal, 2015, vol. 3, No. 5, p. A53, XP002764838.

Bercik et al. "The anxiolytic effect of *Bifidobacterium longum* NCC3001 involves vagal pathways for gut-brain communication" Neurogastroenterol Motil., 2011, vol. 23, No. 12, pp. 1132-1139.

Dinan et al. Neurogastroenterol. Motil., 25:713-719 (2015) (Year: 2015).

(Continued)

*Primary Examiner* — Paul J Holland
(74) *Attorney, Agent, or Firm* — K&L Gates LLP

(57) ABSTRACT

Compositions and methods use *Bifidobacterium longum* NCC3001 (ATCC BAA-999) to stabilize or improve mood, modulate excessive emotional distress, reduce anxiety, and/or reduce stress. In an embodiment, the composition can be administered daily for at least three weeks.

15 Claims, 6 Drawing Sheets

(56) References Cited

OTHER PUBLICATIONS

Liu et al., J. Agric. Food Chem., 63:7885-7895 (2015) (Year: 2015).
Logan et al., Medic. Hypo., 64:533-538 (2005) (Year: 2005).
Slyepchenko et al., CNS Neuro. Dis., 13:1770-1786 (2014) (Year: 2014).
Foster, Cerebrum, 9:1-14 (2013) (Year: 2013).
Foster et al, Trends Neurosci., 36(5):305-312 (2013) (Year: 2013).
Messaoudi et al., Brit. J. Nutr., 105:755-764 (2011) (Year: 2011).
Salminen et al., "Probiotics: How Should They Be Defined?", Trends in Food Science & Technology, vol. 10, 1999, pp. 107-110.
Akkasheh et al., "Clinical and Metabolic Response to Probiotic Administration in Patients with Major Depressive Disorder: A Randomized, Double-Blind, Placebo-Controlled Trial", Nutrition, vol. 32, Issue No. 3, 2016, pp. 315-320.
Odamaki et al., "Influence of *Bifidobacterium longum* BB536 Intake on Faecal Microbiota in Individuals with Japanese Cedar Pollinosis During the Pollen Season", Journal of Medical Microbiology, vol. 56, Issue No. 10, 2007, pp. 1301-1308.
Akatsu et al., "Clinical Effects of Probiotic *Bifidobacterium longum* BB536 on Immune Function and Intestinal Microbiota in Elderly Patients Receiving Enteral Tube Feeding", Journal of Parenteral and Enteral Nutrition, vol. 37, Issue No. 5, 2012, pp. 1-10.
Marcos et al., "The Effect of Milk Fermented by Yogurt Cultures Plus Lactobacillus Casel DN-114001 on the Immune Response of Subjects under Academic Examination Stress", European Journal of Nutrition, vol. 43, Issue No. 6, 2004, pp. 381-389.
Kondo et al., "Modulatory Effects of *Bifidobacterium longum* BB536 on Defecation in Elderly Patients Receiving Enteral Feeding", World Journal of Gastroenterology, vol. 19, Issue No. 14, Apr. 14, 2013, pp. 2162-2170.
Rao et al., "A Randomized, Double-Blind, Placebo-Controlled Pilot Study of a Probiotic in Emotional Symptoms of Chronic Fatigue Syndrome", Gut Pathogens, vol. 1, Issue No. 6, 2009, pp. 1-6.
Nishihira et al., "Elevation of Natural Killer Cell Activity and Alleviation of Mental Stress by the Consumption of Yogurt Containing Lactobacillus Gasseri SBT2055 and *Bifidobacterium longum* SBT2928 in a Double-Blind, Placebo-Controlled Clinical Trial", Journal of Functional Foods, vol. 11, 2014, pp. 261-268.
Zuniga et al., "I.31, A New Combination of Probiotics, Improves Irritable Bowel Syndrome-Related Quality of Life", World Journal of Gastroenterology, vol. 20, Issue No. 26, Jul. 14, 2014, pp. 8709-8716.
Liang et al., "Microorganism and Behavior and Psychiatric Disorders", Advances in Psychological Science, vol. 20, Issue No. 1, Jan. 15, 2012, pp. 75-97.
China Patent Office Communication for Application No. 201680049469.1, mailed on Dec. 9, 2021, 23 Pages.
English Translation of "Natural Biological Therapy: A Guide to Probiotic Health Care and Consumption", Dec. 31, 2006, pp. 58-60.
Ichikawa et al., "Anxiety Disorders and Depression: Drug Choices Based on Condition", Depression Strategy, vol. 3, Issue No. 2, 2013, pp. 4-8.
Office Action Received for Application No. JP2022-103685, mailed on Dec. 12, 2023, 4 Pages of Official Copy.

* cited by examiner

FIG. 3
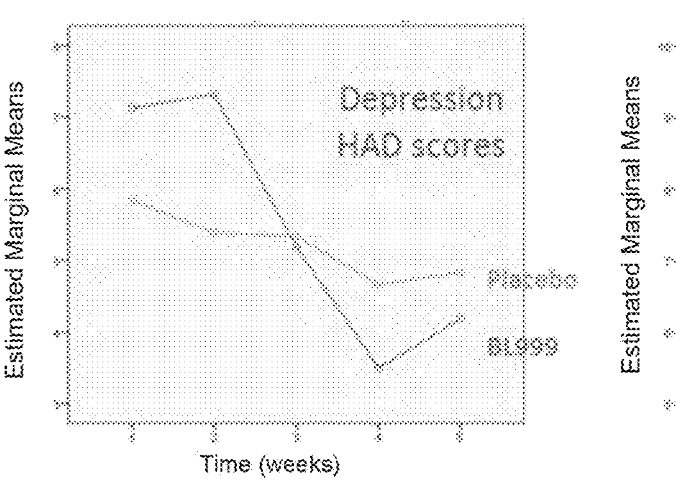
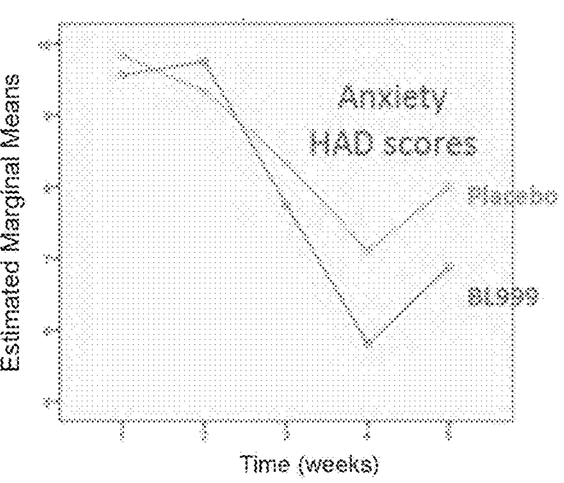

FIG. 4
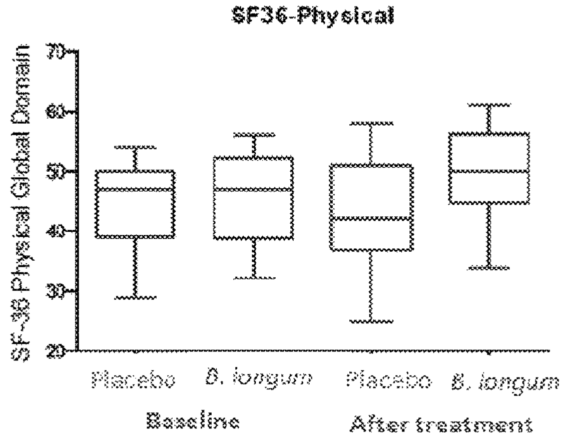
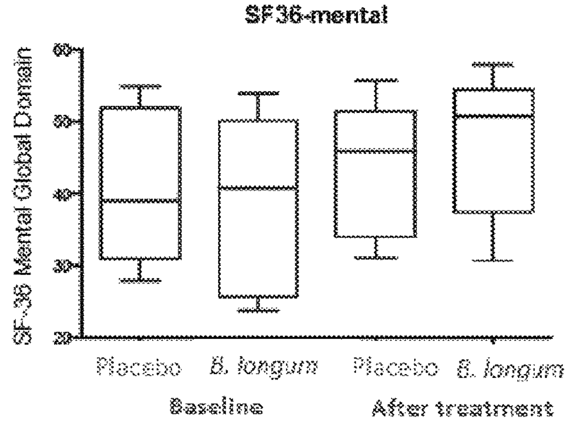

FIG. 5

| | Physical Functioning (PF) Post-Treatment | Role Physical (RP) Post-Treatment | Bodily Pain (BP) Post-Treatment | General health (GH) Post-Treatment | Vitality (VT) Post-Treatment | Social functioning (SF) Post-Treatment | Role emotional (RE) Post-Treatment | Mental Health (MH) Post-Treatment |
|---|---|---|---|---|---|---|---|---|
| Mann-Whitney U | 106.000 | 90.000 | 152.500 | 136.500 | 109.000 | 134.000 | 123.000 | 135.500 |
| Wilcoxon W | 316.000 | 300.000 | 362.500 | 346.500 | 319.000 | 344.000 | 333.000 | 345.500 |
| Z | -1.981 | -2.582 | -.542 | -1.024 | -1.889 | -1.127 | -1.672 | -1.056 |
| Asymp. Sig. (2-tailed) | .047 | .010 | .588 | .306 | .082 | .260 | .084 | .291 |
| Exact Sig. [2*(1-tailed Sig.)] | .052[b] | .014[b] | .536[b] | .311[b] | .065[b] | .283[b] | .133[b] | .297[b] |

a. Grouping Variable: Group b. Not corrected for ties

FIG. 6

Before treatment

After treatment

METHODS AND COMPOSITIONS USING *BIFIDOBACTERIUM LONGUM* TO MODULATE EMOTIONAL REACTIVITY AND TREAT OR PREVENT SUB-CLINICAL MOOD DISTURBANCES

CROSS REFERENCE TO RELATED APPLICATIONS

The present application is a Continuation of U.S. application Ser. No. 15/754,894, filed on Feb. 23, 2018, which is a National Stage of International Application No. PCT/EP2016/070465, filed on Aug. 31, 2016, which claims priority to U.S. Provisional Patent Application No. 62/212,148, filed on Aug. 31, 2015, U.S. Provisional Patent Application No. 62/220,414, filed on Sep. 18, 2015, and U.S. Provisional Patent Application No. 62/236,638, filed on Oct. 2, 2015, the entire contents of which are being incorporated herein by reference.

BACKGROUND

The present disclosure generally relates to probiotic bacteria. Specifically, compositions and methods are disclosed that use *Bifidobacterium longum* NCC3001 (ATCC BAA-999) to stabilize or improve mood and/or modulate excessive emotional distress.

Anxiety disorders affect about 40 million American adults of the age of 18 years and older. This represents on average about 18% of the adult population. A brief period of anxiety can be caused by, for example, stressful events such as examinations or circumstances that are considered as slightly embarrassing. However, anxiety can last much longer, such as at least half a year, and the anxiety conditions can continue to become more severe and crippling if not treated. Anxiety disorders may also occur along with other mental or physical illnesses, including alcohol or substance abuse. Typical anxiety disorders are panic disorder, obsessive-compulsive disorder (OCD), post-traumatic stress disorder (PTSD), social phobia (or social anxiety disorder), specific phobias, and generalized anxiety disorder (GAD).

Some therapies for anxiety-related disorders are available today. In general, anxiety disorders are treated with medication such as antidepressants, anti-anxiety drugs, or beta-blockers. The medications alter brain chemistry and sometimes have severe side effects. The medications can also have undesirable interactions with other frequently taken medications.

SUMMARY

The present inventors surprisingly found that *Bifidobacterium longum* ATCC BAA-999 reduces brain emotional activity in patients to whom these bacteria are administered. As set forth in more detail later herein, the present inventors conducted a randomized, double blind, placebo-controlled trial. Psychopathology (high incidence of anxiety) plays a central role in irritable bowel syndrome (IBS), so this condition was used as a model for the clinical trial. The results demonstrated that six-week treatment with *B. longum* ATCC BAA-999 improved co-morbid depressive symptoms, overall gastrointestinal symptoms, and quality of life in patients with IBS.

Specifically, the study showed that administration of *B. longum* ATCC BAA-999 modulates behavior via gut-to-brain signaling. These effects appear to be mediated through down-regulation of the brain areas involved with the emotion control. Six week treatment with *B. longum* ATCC BAA-999 in patients with non-constipation IBS improved depression scores, achieved adequate relief of IBS symptoms, improved quality of life physical scores, and down-regulated engagement of brain centers involved in the control of emotions and mood (amygdala and fronto-limbic regions) in response to fearful stimuli.

Without wishing to be bound by theory, the inventors presently believe that the underlying prophylactic and/or therapeutic mechanism of the *B. longum* ATCC BAA-999 is related to the modulation of the bidirectional microbial-gut-brain axis, possibly significantly associated with psychological factors. In this regard, IBS is believed to result from the interaction of altered gut physiology and psychological factors via the gut-brain axis, where brain and gut symptoms are reciprocally influencing each other. Intestinal microbiota play a central role in this "dialogue" between the gut and the brain.

Accordingly, in a general embodiment, the present disclosure provides a method of stabilizing and/or improving mood. The method comprises administering an edible composition comprising a therapeutically effective amount of *B. longum* ATCC BAA-999 to an individual in need thereof.

In an embodiment, the method comprises identifying the individual as being in need of stabilized and/or improved mood.

In an embodiment, the composition further comprises an ingredient selected from the group consisting of a fat, a protein, a carbohydrate and combinations thereof.

In an embodiment, the composition comprises a prebiotic. The prebiotic can be selected from the group consisting of an oligosaccharide, a dietary fiber, and a combination thereof.

In an embodiment, the composition is administered to the individual each day of a time period that is at least three weeks.

In an embodiment, at least a portion of the *B. longum* ATCC BAA-999 is alive. The composition can comprise $10^4$ to $10^{11}$ cfu of the *B. longum* ATCC BAA-999 per g of dry weight of the composition. The composition can be administered to the individual in a daily dose comprising between $10^4$ and $10^{12}$ cfu of the *B. longum* ATCC BAA-999. The daily dose can be administered to the individual each day of a time period that is at least three weeks.

In an embodiment, at least a portion of the *B. longum* ATCC BAA-999 is non-replicating cells. The composition can comprise between $10^2$ and $10^8$ of the non-replicating cells of *B. longum* ATCC BAA-999 per g of dry weight of the composition. The composition can be administered to the individual in a daily dose comprising between $10^4$ and $10^{10}$ of the non-replicating cells of *B. longum* ATCC BAA-999. The daily dose can be administered to the individual each day of a time period that is at least three weeks.

In an embodiment, the method is a natural therapy.

In another embodiment, the present disclosure provides a method of modulating excessive emotional distress. The method comprises administering to an individual in need thereof an edible composition comprising a therapeutically effective amount of *B. longum* ATCC BAA-999.

In an embodiment, the individual has a condition selected from the group consisting of a social phobia, a specific phobia, and combinations thereof.

In an embodiment, the method comprises identifying the individual as having excessive emotional distress.

In another embodiment, the present disclosure provides a method of making an edible composition for achieving an effect selected from the group consisting of stabilizing or improving mood, modulating excessive emotional distress, reducing anxiety, reducing stress, and combinations thereof. The method comprises incorporating a therapeutically effective amount or a prophylactically effective amount of *B. longum* ATCC BAA-999 into a food product comprising at least one ingredient selected from the group consisting of a fat, a protein and a carbohydrate.

In another embodiment, the present disclosure provides a method of supplementing a regimen achieving an effect selected from the group consisting of stabilizing mood, improving mood, modulating excessive emotional distress, reducing anxiety, reducing stress, and combinations thereof. The regimen that is supplemented comprises administering to an individual in need or at risk thereof a pharmaceutical composition. The method comprises administering an edible composition comprising a therapeutically effective amount or a prophylactically effective amount of *B. longum* ATCC BAA-999 to the individual, in addition to the pharmaceutical composition.

In another embodiment, the present disclosure provides a composition for achieving an effect selected from the group consisting of stabilizing mood, improving mood, modulating excessive emotional distress, reducing anxiety, reducing stress, and combinations thereof. The composition comprises a therapeutically effective amount or a prophylactically effective amount of *B. longum* ATCC BAA-999.

An advantage of one or more embodiments provided by the present disclosure is a composition comprising a bacterial strain that is effective, readily available, low-priced, and safe to administer without unwanted side effects which can be used to stabilize or improve mood and/or modulate excessive emotional distress.

Another advantage of one or more embodiments provided by the present disclosure is to stabilize or improve mood and/or modulate excessive emotional distress using a bacterial strain that is commercially available and already tested and found to be acceptable for addition to food products.

A further advantage of one or more embodiments provided by the present disclosure is to use a natural therapy to down-regulate the emotional response to fearful stimuli and/or stressful stimuli.

Yet another advantage of one or more embodiments provided by the present disclosure is to use a natural therapy to improve quality of life, in particular vitality and emotional health.

Another advantage of one or more embodiments provided by the present disclosure is to provide a better safety profile relative to known mood-regulating compounds.

A further advantage of one or more embodiments provided by the present disclosure is to minimize or avoid completely the side effects from known mood-regulating compounds.

An additional advantage of one or more embodiments provided by the present disclosure is to improve the effect of and/or reduce the dose of one or more known mood-regulating compounds which are co-administered with the composition disclosed herein.

Yet another advantage of one or more embodiments provided by the present disclosure is to minimize or avoid completely unnecessary costs related to healthcare assistance.

A further advantage of one or more embodiments provided by the present disclosure is to use to stabilize or improve mood and/or modulate excessive emotional distress using a bacterial strain that provides other health benefits as well.

Additional features and advantages are described herein and will be apparent from the following Detailed Description and the Figures.

BRIEF DESCRIPTION OF THE FIGURES

FIG. 3 shows graphs demonstrating the secondary outcome from administration of *B. longum* ATCC BAA-999, improvement in depression and anxiety continuous scores.

FIGS. 4 and 5 respectively show graphs and a table demonstrating that administration of *B. longum* ATCC BAA-999 significantly improved the physical global domain as well as general physical health (physical functioning) and problems with work of other daily activities (role physical) and resulted in an improvement trend in the mental subdomains of vitality and role emotional.

FIG. 6 shows fMRI images demonstrating greater engagement of the visual association and parietal cortices in the group administered *B. longum* ATCC BAA-999 relative to the placebo group and lesser engagement of brain centers involved in emotion and mood (amygdala and fronto-limbic region) in the group administered *B. longum* ATCC BAA-999 relative to the placebo group.

DETAILED DESCRIPTION

Figure 1:
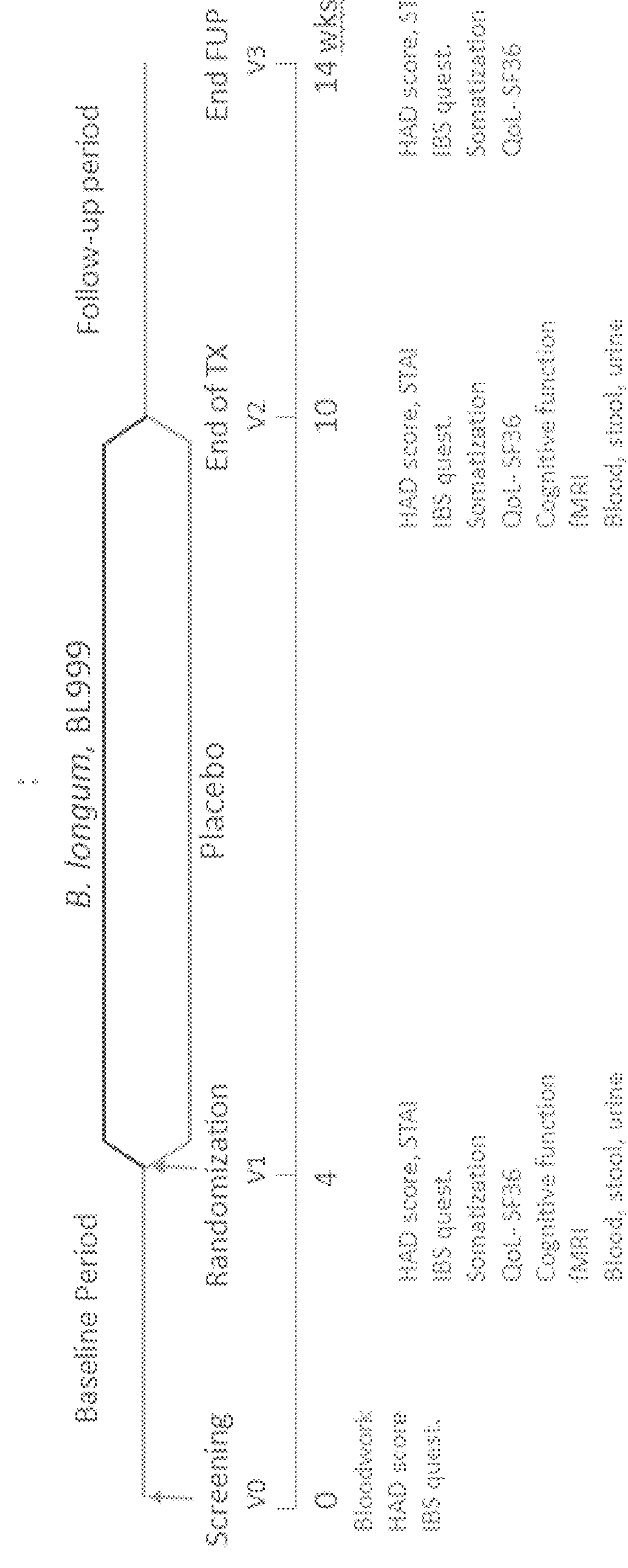
FIG. 1 shows the design of the clinical trial disclosed herein.

As used in this disclosure and the appended claims, the singular forms "a," "an" and "the" include plural referents unless the context clearly dictates otherwise. Thus, for example, reference to "a bacterial strain" or "the bacterial strain" includes two or more bacterial strains.

The words "comprise," "comprises" and "comprising" are to be interpreted inclusively rather than exclusively. Likewise, the terms "include," "including" and "or" should all be construed to be inclusive, unless such a construction is clearly prohibited from the context.

Nevertheless, the compositions disclosed herein may lack any element that is not specifically disclosed. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive. Any embodiment disclosed herein can be combined with any other embodiment disclosed herein unless explicitly stated otherwise.

As used herein, "about" and "approximately" are understood to refer to numbers in a range of numerals, for example the range of −10% to +10% of the referenced number, preferably within −5% to +5% of the referenced number, more preferably within −1% to +1% of the referenced number, most preferably within −0.1% to +0.1% of the referenced number.

Furthermore, all numerical ranges herein should be understood to include all integers, whole or fractions, within the range. The term "between" includes the end points of the identified range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

"Animal" includes, but is not limited to, mammals, which includes but is not limited to, rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the terms "individual" and "patient" are understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human that can benefit from the treatment.

The terms "treatment" and "treating" include any effect that results in the improvement of the condition or disorder, for example lessening, reducing, modulating, or eliminating the condition or disorder. The term does not necessarily imply that a subject is treated until total recovery. Non-limiting examples of "treating" or "treatment of" a condition or disorder include: (1) inhibiting the condition or disorder, i.e. arresting the development of the condition or disorder or its clinical symptoms and (2) relieving the condition or disorder, i.e. causing the temporary or permanent regression of the condition or disorder or its clinical symptoms. A treatment can be patient- or doctor-related.

The terms "prevention" or "preventing" mean causing the clinical symptoms of the referenced condition or disorder to not develop in an individual that may be exposed or predisposed to the condition or disorder but does not yet experience or display symptoms of the condition or disorder. The terms "condition" and "disorder" mean any disease, condition, symptom, or indication.

The relative terms "improved," "increased," "enhanced" and the like refer to the effects of the composition comprising *B. longum* ATCC BAA-999 (disclosed herein) relative to a composition lacking *B. longum* ATCC BAA-999 but otherwise identical.

The terms "food," "food product" and "food composition" mean a product or composition that is intended for ingestion by an individual such as a human and provides at least one nutrient to the individual. The compositions of the present disclosure, including the many embodiments described herein, can comprise, consist of, or consist essentially of the essential elements and limitations described herein, as well as any additional or optional ingredients, components, or limitations described herein or otherwise useful in a diet.

As used herein, "complete nutrition" contains sufficient types and levels of macronutrients (protein, fats and carbohydrates) and micronutrients to be sufficient to be a sole source of nutrition for the animal to which the composition is administered. Individuals can receive 100% of their nutritional requirements from such complete nutritional compositions.

An aspect of the present disclosure is a composition comprising *B. longum* ATCC BAA-999 in an amount effective to stabilize or improve mood and/or modulate excessive emotional distress (e.g. prevent or treat a phobia) in an individual, preferably a human. *B. longum* ATCC BAA-999 is also known as BL999 and NCC3001 and may be obtained commercially from specialist suppliers, for example from Morinaga Milk Industry Co. Ltd. of Japan under the trademark BB536. The term "*B. longum* ATCC BAA-999" includes the bacterium, parts of the bacterium, and/or a growth medium fermented by the bacterium. In an embodiment, the composition can be administered to the individual daily for a time period that is at least three weeks, at least four weeks in some embodiments, at least five weeks in other embodiments, and at least six weeks in yet other embodiments.

In some embodiments, the method is a natural therapy. For example, the composition can consist of natural ingredients, and preferably the individual is not administered any artificial composition such as a synthetic pharmaceutical compound. In other embodiments, the composition supplements a regimen in which a pharmaceutical composition is also administered.

As noted above, the composition can be administered to stabilize and/or improve mood. The term "mood" refers to a state or quality of feeling (an emotional state) at a particular time. Moods differ from simple emotions in that they are less specific, less intense, and less likely to be triggered by a particular stimulus or event. Moods generally have either a positive or negative valence. An improved mood may comprise one or more of a decreased depressive level, a decreased anxiety level, a decreased stress level, an increased perceived energy level ("vitality"), a more positive emotional state, an increased self-esteem, a reduced amount and/or a reduced intensity of negative thoughts and/or negative tensions, a reduced risk of mood swings, or retention of a positive mood. Clinical depression and bipolar disorder are examples of mood disorders (i.e., long-term disturbances of mood); mood disorders are a group of diagnoses in the classification system of the Diagnostic and Statistical Manual of Mental Disorders (DSM) where disturbances in mood are the main underlying feature.

Non-limiting examples of an individual in need of an improved mood include an individual engaging in substance abuse; an individual recovering from substance abuse; an individual consuming a benzodiazepine, for example daily for at least six months; and combinations thereof.

Further in this regard, the composition can be administered to reduce anxiety and/or to reduce stress in an individual in need thereof. The method can comprise identifying the individual as being in need of reduced anxiety and/or reduced stress.

As used herein, "substance abuse" is use of any substance in which the user consumes the substance in amounts or with methods neither approved nor supervised by medical professionals. An individual engaging in substance abuse typically has consumed the substance within the last month, within the last week, or within the last day. An individual recovering from substance abuse typically has engaged in substance abuse within the last ten years, the last five years, the last four years, the last three years, the last two years or even within the last year but has not engaged in substance abuse for at least a week, preferably at least a month and more preferably at least a year.

Non-limiting examples of substances included in "substance abuse" are nicotine, khat, cannabis, alcohol, gamma-hydroxybutyric acid (GHB), flunitrazepam, alkyl nitrates, 3,4-methylenedioxy-N-methylamphetamine (MDMA or ecstasy), lysergic acid diethylamide (LSD), opiates (including opioids), mescaline, psilocybin, methylphenidate, 4-methylthioamphetamine (4-MTA), buprenorphine, amphetamine, methamphetamine, ketamine, tiletamine, phencyclidine (PCP), salvia, dextromethorphan (DXM), benzodiazepines, barbituates, sleep medication, cocaine, heroin, solvents, gases, and anabolic steroids.

"Alcohol" includes any substance containing ethyl alcohol. Non-limiting examples of "alkyl nitrates" include isoamyl nitrite, isopentyl nitrite, cyclohexyl nitrite, isobutyl nitrite, isopropyl nitrite, and butyl nitrite. By "opiate" is meant any preparation or derivative of opium, which is a naturally occurring substance extracted from the seed pod of a poppy plant (e.g., *Papaver somniferum*) and which contains at least one of a number of alkaloids including morphine, noscapine, codeine, papaverine, or thebaine. Heroin is processed from morphine. For the purposes of the present disclosure, the term opiate includes opioids. Non-limiting examples of opiates include codeine, oxycodone, hydrocodone, oxymorphone, meperidine, propoxyphene, morphine, methadone, fentanyl, and analogs thereof. Non-limiting examples of "solvents" include paint thinners, gasoline, and glues, and non-limiting examples of "gases" include butane, propane, aerosol propellants, and nitrous oxide.

Accordingly, some embodiments of the methods of stabilizing and/or improving mood disclosed herein comprise diagnosing the individual as having a need for stabilized and/or improved mood, e.g., before initiating administration of the composition comprising *B. longum* ATCC BAA-999.

As noted above, the composition can be administered to modulate excessive emotional distress (e.g. prevent or treat a phobia). A "phobia" is a persistent fear of an object or situation which the individual expends effort to avoid disproportionally to the actual danger posed. Non-limiting examples of a "phobia" that can be treated or prevented by the composition disclosed herein include a social phobia (e.g., a social anxiety disorder), a specific phobia (e.g., a fear of a particular animal type, a fear of a particular environment type such as heights, a fear of a particular situation such as a small confined space, and/or a fear of a particular medical procedure) and combinations thereof. Accordingly, some embodiments of the methods of modulating excessive emotional distress disclosed herein comprise diagnosing the individual having excessive emotional distress, e.g., before initiating administration of the composition comprising *B. longum* ATCC BAA-999.

*B. longum* ATCC BAA-999 was deposited by the Assignee of the present application as NCC 3001 on Jan. 29, 2001 at the Institut Pasteur, 28 rue du Docteur Roux, F-75024 Paris Cedex 15, France. All restrictions upon public access to the deposits will be irrevocably removed upon grant of a patent on this application, and the deposits will be replaced if viable samples cannot be dispensed by the depository.

The *B. longum* ATCC BAA-999 may be cultured according to any suitable method. *B. longum* ATCC BAA-999 may be added to a food product in a freeze-dried or spray-dried form, for example, to form the composition.

The composition may be orally and/or enterally administrable; for example in the form of a powder for reconstitution with milk or water. The composition may be selected from the group consisting of a food composition, a pet food composition, a dietary supplement, a nutraceutical, a nutritional formula, a drink, and a medical composition. In a preferred embodiment, the composition is a food product intended for an adult such as a human adult.

A food composition has the advantage that such a composition can be distributed in not only pharmacies and drug stores but also in supermarkets. The generally pleasant taste of food compositions will further contribute to the acceptance of the product. Non-limiting examples of suitable food compositions include yogurts, milk, flavored milk, ice cream, ready-to-eat desserts, malt drinks, ready-to-eat dishes, instant dishes, drinks for humans, and food compositions representing a complete or a partial diet.

The composition may further contain one or more of the following: a protective hydrocolloid (such as a gum, a protein, a modified starch), a binder, a film-forming agent, an encapsulating agent, a wall/shell material, a matrix compound, a coating, an emulsifier, a surface active agent, a solubilizing agent (such as an oil, a fat, a wax, a lecithin), an adsorbent, a carrier, a filler, a co-compound, a dispersing agent, a wetting agent, a processing aid (such as a solvent), a flowing agent, a taste masking agent, a weighting agent, a jellifying agent, a gel forming agent, an antioxidant or an antimicrobial. The composition may also contain a conventional pharmaceutical additive, adjuvant, excipient or diluent, including, but not limited to, water, gelatin of any origin, vegetable gum, ligninsulfonate, talc, a sugar, a starch, gum arabic, a vegetable oil, polyalkylene glycol, a flavoring agent, a preservative, a stabilizer, a, emulsifying agent, a buffer, a lubricant, or a colorant. Such further components are preferably selected having regard to their suitability for the intended recipient. In an embodiment, the composition is a nutritionally complete formula.

The composition can comprise a protein. Non-limiting examples of suitable proteins include animal proteins (such as milk protein, meat protein or egg protein), a vegetable protein (such as soy protein, wheat protein, rice protein, or pea protein); mixtures of free amino acids; or combinations thereof. Milk proteins such as casein and whey, and soy proteins are particularly preferred.

The proteins may be intact, hydrolyzed, or a mixture of intact and hydrolyzed proteins. Partially hydrolyzed proteins (degree of hydrolysis between 2 and 20%) may be advantageous for human subjects and/or animals at risk of developing cows' milk allergy. Furthermore, pre-hydrolyzed protein sources are generally easier digested and absorbed by an impaired gastro-intestinal tract.

If hydrolyzed proteins are used, the hydrolysis process may be carried out as desired and as known in the art. For example, a whey protein hydrolysate may be prepared by enzymatically hydrolyzing the whey fraction in one or more steps. If the whey fraction used as the starting material is substantially lactose-free, the protein can suffer much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The composition may also contain a carbohydrate and/or a source of fat. If the composition includes a fat, the fat preferably provides 5% to 40% of the energy of the composition; for example 20% to 30% of the energy. A suitable fat profile may be obtained using a blend of canola oil, corn oil and high-oleic acid sunflower oil.

The carbohydrate preferably provides 40% to 80% of the energy of the composition. Non-limiting examples of suitable carbohydrates include sucrose, lactose, glucose, fructose, corn syrup solids, maltodextrins, and mixtures thereof. Additionally or alternatively, a dietary fiber may be added. Dietary fiber passes through the small intestine undigested by enzymes and functions as a natural bulking agent and laxative. Dietary fiber may be soluble or insoluble and generally a blend of the two types is preferred. Non-limiting examples of suitable dietary fibers include soy, pea, oat, pectin, guar gum, partially hydrolyzed guar gum, gum Arabic, fructo-oligosaccharides, acidic oligosaccharides, galacto-oligosaccharides, sialyl-lactose and oligosaccharides derived from animal milks. A preferred fiber blend is a mixture of inulin with shorter chain fructo-oligosaccharides. In an embodiment, the fiber content is between 2 and 40 g/L of the composition, for example between 4 and 10 g/L.

The composition may comprise minerals and/or micronutrients such as trace elements and vitamins in accordance with the recommendations of Government bodies such as the USRDA. For example, the composition may comprise, per daily dose, one or more of the following micronutrients, preferably in the ranges given: 300 to 500 mg calcium, 50 to 100 mg magnesium, 150 to 250 mg phosphorus, 5 to 20 mg iron, 1 to 7 mg zinc, 0.1 to 0.3 mg copper, 50 to 200 μg iodine, 5 to 15 μg selenium, 1000 to 3000 μg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 μg Vitamin B12, 100 to 800 μg folic acid, 30 to 70 μg biotin, 1 to 5 μg Vitamin D, and/or 3 to 10 μg Vitamin E.

One or more food grade emulsifiers may be incorporated into the composition, such as diacetyl tartaric acid esters of mono- and di-glycerides, lecithin, and/or mono- and di-glycerides. Suitable salts and stabilizers may be included.

In an embodiment, the composition comprises an additional food grade micro-organism (i.e., in addition to the *B. longum* ATCC BAA-999). "Food grade" micro-organisms are micro-organisms that are safe for use in food. The food grade micro-organisms can comprise food-grade yeast. The food grade bacteria may be selected from the group consisting of lactic acid bacteria, bifidobacteria, propionibacteria and mixtures thereof. Non-limiting examples of suitable food grade yeast include *Saccharomyces cerevisiae* and/or *Saccharomyces boulardii.*

The food grade bacteria can comprise additional probiotic bacteria, although in some embodiments the *B. longum* ATCC BAA-999 is the only probiotic bacteria in the composition. "Probiotic" means microbial cell preparations or components of microbial cells with a beneficial effect on the health or well-being of the host. (Salminen S., Ouwehand A., Benno Y. et al "Probiotics: how should they be defined" Trends Food Sci. Technol. 1999: 10 107-10).

Probiotic bacteria are preferably selected from the group consisting of lactic acid bacteria, bifidobacteria, propionibacteria and mixtures thereof. Probiotic bacteria may be any lactic acid bacteria or bifidobacteria with established probiotic characteristics. For example, probiotic bacteria may be capable of promoting the development of a bifidogenic intestinal microbiota.

Non-limiting examples of suitable probiotic bacteria include *Bifidobacterium, Lactobacillus, Streptococcus, Saccharomyces* and mixtures thereof, in particular selected from the group consisting of *Bifidobacterium longum, Bifidobacterium lactis, Lactobacillus acidophilus, Lactobacillus rhamnosus, Lactobacillus paracasei, Lactobacillus johnsonii, Lactobacillus plantarum, Lactobacillus salivarius, Enterococcus faecium, Saccharomyces boulardii* and *Lactobacillus reuteri* and mixtures thereof, preferably selected from the group consisting of *Lactobacillus johnsonii* (NCC533; CNCM 1-1225), *Bifidobacterium longum* (NCC490; CNCM 1-2170), *Bifidobacterium longum* (NCC2705; CNCM 1-2618), *Bifidobacterium lactis* (2818; CNCM 1-3446), *Lactobacillus paracasei* (NCC2461; CNCM 1-2116), *Lactobacillus rhamnosus* GG (ATCC53103), *Lactobacillus rhamnosus* (NCC4007; CGMCC 1.3724), *Enterococcus faecium* SF 68 (NCIMB10415), and mixtures thereof.

In a preferred embodiment, the composition comprises at least one prebiotic. "Prebiotic" means a food substance intended to promote the growth of probiotic bacteria in the intestines. A prebiotic can promote the growth of certain food grade bacteria, in particular growth of probiotic bacteria, in the intestines and can thus enhance the effect of *B. longum* ATCC BAA-999 and any additional probiotic bacteria. Preferably the prebiotic is selected from the group consisting of oligosaccharides and optionally fructose, galactose, mannose, soy and/or inulin; dietary fibers; or mixtures thereof.

At least a portion of the *B. longum* ATCC BAA-999 may be living bacterium. Additionally or alternatively, at least a portion of the *B. longum* ATCC BAA-999 may be inactivated non-replicating bacterium.

"Non-replicating" means that no viable cells and/or colony forming units can be detected by classical plating methods. Such classical plating methods are summarized in the microbiology book: James Monroe Jay, Martin J. Loessner, David A. Golden. 2005. Modem food microbiology. 7th edition, Springer Science, New York, N.Y. 790 p. Typically, the absence of viable cells can be shown as follows: no visible colony on agar plates or no turbidity in liquid growth medium after inoculation with different concentrations of bacterial preparations ("non-replicating" samples) and incubation under appropriate conditions (aerobic and/or anaerobic atmosphere for at least 24 h). In some embodiments, such as special sterile food products or medicaments, a non-replicating form of the *B. longum* ATCC BAA-999 may be preferable. For example, at least 80%, preferably at least 90%, more preferably at least 95% of the *B. longum* ATCC BAA-999 can be non-replicating in the composition.

In an embodiment, at least a part of the *B. longum* ATCC BAA-999 are alive in the composition and preferably arrive alive in the intestine. For example, at least 5%, preferably at least 10%, more preferably at least 15% of the *B. longum* ATCC BAA-999 can be viable in the composition. As a result, the alive *B. longum* ATCC BAA-999 can persist in the intestine and may increase their effectiveness by multiplication. The alive *B. longum* ATCC BAA-999 may also be effective by interacting with the commensal bacteria and/or the host.

In therapeutic applications, the composition is administered in an amount sufficient to at least partially cure or arrest the symptoms of the condition and its complications. An amount adequate to accomplish this purpose is defined as "a therapeutically effective dose". Amounts effective for this purpose will depend on a number of factors known to those of skill in the art, such as the severity of the condition and the weight and general state of the patient.

In prophylactic applications, the composition can be administered to a patient susceptible to or otherwise at risk of a particular condition in an amount that is sufficient to at least partially reduce the risk of developing the condition. Such an amount is "a prophylactically effective dose." Again, the precise amounts depend on a number of patient-specific factors, such as the patient's state of health and weight.

The composition is preferably administered in an amount that provides a therapeutically effective dose and/or in a prophylactic effective dose of the *B. longum* ATCC BAA-999. If at least a portion of the *B. longum* ATCC BAA-999 is present in a viable form, the *B. longum* ATCC BAA-999 is theoretically effective in any concentration because the *B. longum* ATCC BAA-999 can colonize the gut and multiply therein.

Nevertheless, a daily dose of the composition preferably provides between $10^4$ and $10^{12}$ cfu (colony forming units) of the *B. longum* ATCC BAA-999, more preferably from $10^4$ to $10^{11}$ cfu, most preferably from $10^4$ to $10^{10}$ cfu. The composition may comprise between $10^2$ and $10^{10}$ cfu, preferably $10^2$ to $10^9$ cfu, more preferably $10^2$ to $10^8$ cfu of the *B. longum* ATCC BAA-999 per gram dry weight of the composition.

In the case of inactivated and/or non-replicating *B. longum* ATCC BAA-999, the composition can comprise between $10^2$ and $10^{10}$ non-replicating cells of the *B. longum* ATCC BAA-999 per gram of dry weight of the composition, preferably $10^3$ to $10^8$ non-replicating cells per gram of dry weight of the composition, more preferably $10^5$ to $10^8$ non-replicating cells per gram of dry weight of the composition.

Non-replicating micro-organisms do not form colonies, so the term "cells" indicates the amount of non-replicating micro-organisms obtained from the specified amount of replicating bacterial cells. This amount includes micro-organisms that are inactivated, non-viable or dead, or present as fragments such as DNA or cell wall materials.

The composition may be a powder having a water activity less than 0.2, preferably less than 0.15. The composition may be a shelf-stable powder. The low water activity can provide this shelf stability and can ensure that the *B. longum* ATCC BAA-999 and any additional probiotic micro-organism will remain viable even after long storage times. Water activity ($a_w$) is a measurement of the energy status of the water in a system and is defined as the vapor pressure of water divided by that of pure water at the same temperature; therefore, pure distilled water has a water activity of exactly one.

Additionally or alternatively, the *B. longum* ATCC BAA-999 and any additional probiotic micro-organism may be provided in an encapsulated form. Encapsulation of the bacteria can have therapeutical and technical advantages. For example, encapsulation can increase the survival of the bacteria and thus the number of live bacteria which arrive in the intestine. Furthermore, the bacteria can be gradually released, allowing a prolonged action of the bacteria on the health of the subject. For example, the bacteria may be freeze or spray dried and incorporated into a gel.

Another aspect of the present disclosure is a method of making an edible composition for stabilizing or improving mood and/or modulating excessive emotional distress. The method can comprise incorporating a therapeutically effective or a prophylactically effective amount of *B. longum* ATCC BAA-999 into a food product comprising at least one of a protein, a fat or a carbohydrate. The food product can be nutritionally complete.

EXAMPLE

The following non-limiting example is a randomized, double blind, placebo-controlled trial illustrative of *B. longum* ATCC BAA-999 reducing brain emotional reactivity.

Introduction: Specific probiotic bacteria can improve gut symptoms of IBS, however, their efficacy in treating co-morbid anxiety or a depressive symptom in this population is unknown. *B. longum* ATCC BAA-999 was previously shown to normalize anxiety-like behavior and hippocampal neurotrophin levels in murine models of low-grade gut inflammation. The present inventors also have unpublished data in depression models in mice and also showing improved sleeping patterns in mice.

Aims & Methods: To evaluate the effects of *B. longum* ATCC BAA-999 on anxiety and depressive symptoms in patients with IBS and to study the underlying mechanisms, the present inventors conducted a randomized, double-blind, placebo-controlled, single center study in adult patients with IBS with diarrhea or mixed stool pattern (Rome III criteria) and mild to moderate anxiety and/or a depressive symptom. There were no differences in demographics and baseline data between the two groups, except for HAD-D scores, which were higher in *B. longum* group (p=0.046).

*B. longum* ATCC BAA-999 (1.0E+10 CFU daily) or placebo (maltodextrin) was administered daily for six weeks. Validated questionnaires were used to assess anxiety and a depressive symptom (HAD score (Hospital Anxiety and Depression) and STAI (State-Trait Anxiety Inventory) score), IBS symptoms (adequate relief question, IBS Birmingham and Bristol scale), quality of life (SF-36) and somatization (PHQ-15) before administration, at the end of administration, and one month after the treatment (follow-up). This experimental design is shown in FIG. 1.

The present inventors assessed brain activation patterns using the backward masked fear paradigm (fMRI), cognitive function (memory and concentration), serum BDNF and inflammatory markers, and gut microbiota profiles (16S rRNA Illumina). The fMRI paradigm utilized Blood Oxygenation Level Dependent (BOLD) activation in response to the presentation of emotional stimuli (fear and happy faces) that were masked by a neutral face, measured over four consecutive fMRI scan acquisitions in the scanner. The amygdala was selected as a priori region of interest. This analysis was performed on all subjects.

Results: The present inventors randomized 44 patients, and 38 of them (*B. longum* ATCC BAA-999=18, placebo=20) completed the study. The results are shown in FIGS. 2-6. At six weeks, depression scores improved in patients treated with *B. longum* ATCC BAA-999 compared with placebo (RR 2.94, 95% CI 1.05-8.23, p=0.01), and this beneficial effect was maintained at follow-up. More patients treated with *B. longum* ATCC BAA-999 than placebo reported adequate relief of overall IBS symptoms (RR 2.1, 95% CI 1.15-3.83, p=0.02) but no statistically significant changes were found in the IBS Birmingham scores. The physical subdomain of quality of life improved in the group treated with *B. longum* ATCC BAA-999 compared with placebo (p=0.03, Mann-Whitney U=228.5), with trends for improvement in the mental subdomains of vitality and emotional role functioning.

The beneficial effect of *B. longum* ATCC BAA-999 on a depressive symptom was maintained at one month post-treatment, while IBS symptoms and quality of life returned to baseline.

Figure 2:
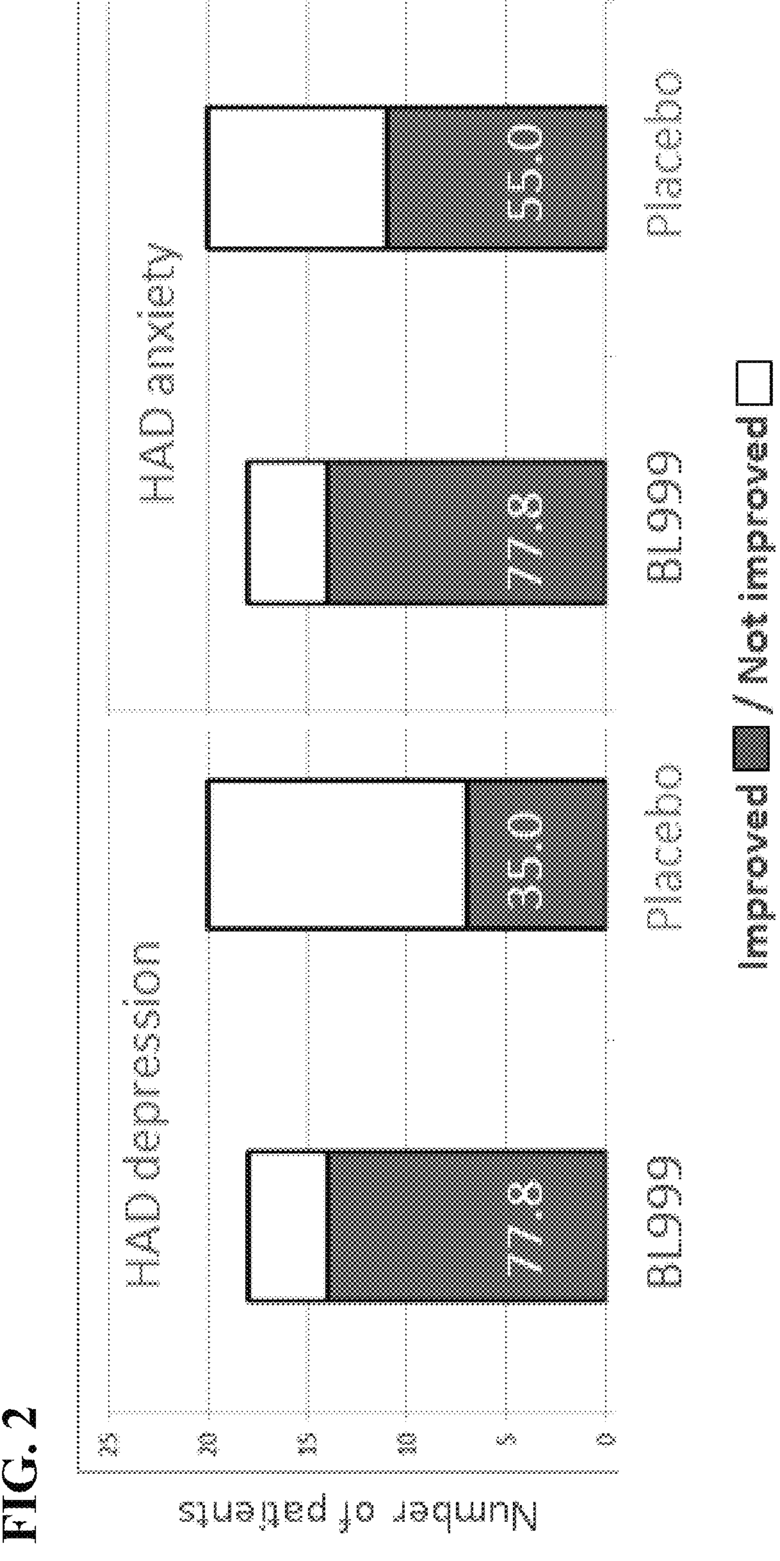
FIG. 2 shows graphs demonstrating the primary outcome from administration of *B. longum* ATCC BAA-999, improvement in depression and anxiety dichotomous scores.

Specifically, FIG. 2 shows that treatment with *B. longum* ATCC BAA-999 improved depression scores both by intention-to-treat analysis (ITT) and per protocol analysis (PP). The beneficial effect of the *B. longum* ATCC BAA-999 was maintained at one month post-treatment (follow-up visit, with both ITT and PP analysis).

FIG. 3 shows that, adjusting for baseline, depression improvement as a continuous variable was achieved in the *B. longum* ATCC BAA-999 group (ANCOVA, p=0.049). This beneficial effect was not maintained at one month post-treatment. Treatment with *B. longum* ATCC BAA-999 did not improve anxiety scores when analyzed as continuous variables.

FIGS. 4 and 5 show that there was a statistically significant improvement in SF-36 physical global domain, as well as in general physical health (Physical functioning) and problems with work or other daily activities (Role physical), in the *B. longum* ATCC BAA-999 compared to placebo. Non-significant differences between treatment groups were observed in SF-36 mental global domain. However, when analyzing the mental subdomains, non-statistically significant trends for improvement in Vitality and Role emotional were observed in the *B. longum* ATCC BAA-999 treated group.

Figure 6:
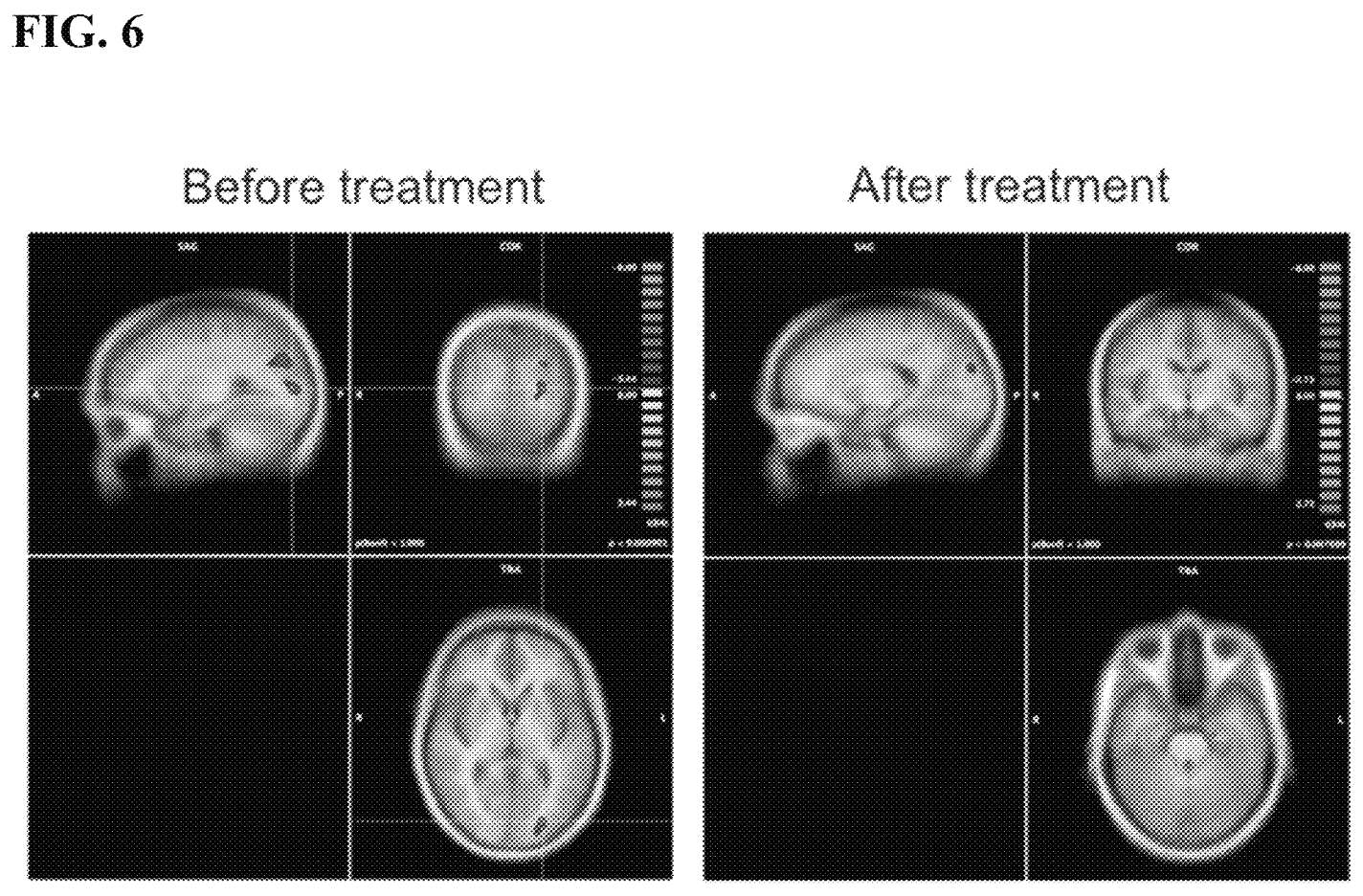

FIG. 6 shows that functional MRI revealed significant reductions from baseline in response to negative emotional stimuli in multiple brain areas involved in emotion processing, including amygdala, frontal and temporal brain regions ($p<0.001$), in patients treated with *B. longum* ATCC BAA-999 compared with placebo. Specifically, before treatment, there was no major difference in response to fear stimuli vs fixation between placebo and *B. longum* groups, except for greater engagement of the visual association and parietal cortices in *B. longum* group. However, at the end of the treatment, there was greater engagement of the amygdala, frontal, and temporal cortices and reduced engagement of occipital regions in placebo group.

No statistically significant differences were observed in anxiety, cognitive function, inflammatory markers, serum BDNF levels or gut microbiota profiles in patients treated with *B. longum* ATCC BAA-999 compared to placebo.

Conclusion: The results demonstrate that a six-week treatment with *B. longum* ATCC BAA-999 improves co-morbid depressive symptoms, overall gastrointestinal symptoms and quality of life in patients with IBS. This effect is associated with changes in the brain activation patterns in the amygdala and fronto-limbic regions, suggesting that reduction in limbic reactivity may underlie the beneficial effect of *B. longum* ATCC BAA-999.

The invention is claimed as follows:

1. A method of stabilizing and/or improving a mood disorder, wherein the mood disorder is clinical depression or bipolar disorder, the method comprising administering to an individual in need thereof an edible composition comprising a therapeutically effective amount of *Bifidobacterium longum* ATCC BAA-999, wherein the stabilizing and/or improving the mood disorder is relative to a level before initiating administration of the edible composition.

2. The method of claim 1, further comprising identifying the individual as being in need of stabilized and/or improved mood before administering the edible composition to the individual.

3. The method of claim 1, wherein the edible composition further comprises an ingredient selected from the group consisting of a fat, a protein, a carbohydrate and combinations thereof.

4. The method of claim 1, wherein the edible composition further comprises a prebiotic.

5. The method of claim 4, wherein the prebiotic is selected from the group consisting of an oligosaccharide, a dietary fiber, and a combination thereof.

6. The method of claim 1, wherein the edible composition is administered to the individual each day of a time period that is at least three weeks.

7. The method of claim 1, wherein at least a portion of the *B. longum* ATCC BAA-999 is alive.

8. The method of claim 7, wherein the edible composition comprises $10^4$ to $10^{11}$ cfu of the *B. longum* ATCC BAA-999 per g of dry weight of the edible composition.

9. The method of claim 7, wherein the edible composition is administered to the individual in a daily dose comprising between $10^4$ and $10^{12}$ cfu of the *B. longum* ATCC BAA-999.

10. The method of claim 9, wherein the daily dose is administered to the individual each day of a time period that is at least three weeks.

11. The method of claim 1, wherein at least a portion of the *B. longum* ATCC BAA-999 is non-replicating cells.

12. The method of claim 11, wherein the edible composition comprises between $10^2$ and $10^8$ of the non-replicating cells of *B. longum* ATCC BAA-999 per g of dry weight of the edible composition.

13. The method of claim 11, wherein the edible composition is administered to the individual in a daily dose comprising between $10^4$ and $10^{10}$ of the non-replicating cells of *B. longum* ATCC BAA-999.

14. The method of claim 13, wherein the daily dose is administered to the individual each day of a time period that is at least three weeks.

15. The method of claim 1, wherein the edible composition consists of natural ingredients.

* * * * *